United States Patent
Huang (10) Patent No.: US 12,083,135 B2
(45) Date of Patent: Sep. 10, 2024

(54) USE OF A NITROGEN-CONTAINING BISPHOSPHONATE IN COMBINATION WITH A GLUCOCORTICOID IN PREVENTING OR TREATING VIRAL PNEUMONIA

(71) Applicant: INSTITUTE OF BASIC MEDICAL SCIENCES, CHINESE ACADEMY OF MEDICAL SCIENCES, Beijing (CN)

(72) Inventor: Bo Huang, Beijing (CN)

(73) Assignee: Institute of Basic Medical Sciences, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 17/720,255

(22) Filed: Apr. 13, 2022

(65) Prior Publication Data
US 2023/0149429 A1 May 18, 2023

(30) Foreign Application Priority Data
Nov. 18, 2021 (CN) .......................... 202111368291.6

(51) Int. Cl.
*A61K 31/663* (2006.01)
*A61K 9/00* (2006.01)
(Continued)

(52) U.S. Cl.
CPC .......... *A61K 31/663* (2013.01); *A61K 9/0019* (2013.01); *A61K 9/0043* (2013.01);
(Continued)

(58) Field of Classification Search
CPC ............... A61K 2300/00; A61K 31/56; A61K 31/569; A61K 31/57; A61K 31/573;
(Continued)

(56) References Cited

FOREIGN PATENT DOCUMENTS

| CN | 114028571 B | 4/2023 | |
| WO | WO-2021207047 A1 * | 10/2021 | ............. A61K 31/59 |

OTHER PUBLICATIONS

Kino et al. (Int. J. Mol. Sci. 2021, 22, 6764, pp. 1-18) (Year: 2021).*
(Continued)

*Primary Examiner* — Savitha M Rao
(74) *Attorney, Agent, or Firm* — Rodney J. Fuller; BOOTH UDALL FULLER, PLC (57) ABSTRACT

Provided is use of a nitrogen-containing bisphosphonate in combination with a glucocorticoid in preventing or treating viral pneumonia. Specifically, provided is a nitrogen-containing bisphosphonate in combination with a glucocorticoid for use in treating or ameliorating coronavirus infections, the nitrogen-containing bisphosphonate is selected from the group consisting of pamidronate, alendronate, risedronate, ibandronate, zoledronate, minodronate and incadronate. The glucocorticoid is selected from the group consisting of dexamethasone, rimexolone, prednisolone, fluorometholone, hydrocortisone, mometasone, fluticasone, beclomethasone, flunisolide, triamcinolone, fluticasone propionate, beclomethasone dipropionate, budesonide and mometasone furoate.

14 Claims, 8 Drawing Sheets

(51) Int. Cl.
| | | |
|---|---|---|
| *A61K 31/569* | (2006.01) | |
| *A61K 31/573* | (2006.01) | |
| *A61K 31/575* | (2006.01) | |
| *A61K 31/58* | (2006.01) | |
| *A61K 31/675* | (2006.01) | |
| *A61P 31/14* | (2006.01) | |
| *A61P 37/06* | (2006.01) | |

(52) U.S. Cl.
CPC .......... *A61K 31/569* (2013.01); *A61K 31/573* (2013.01); *A61K 31/575* (2013.01); *A61K 31/58* (2013.01); *A61K 31/675* (2013.01); *A61P 31/14* (2018.01); *A61P 37/06* (2018.01)

(58) Field of Classification Search
CPC .... A61K 31/575; A61K 31/58; A61K 31/663; A61K 31/675; A61K 9/0019; A61K 9/0043; A61P 11/00; A61P 31/12; A61P 31/14; A61P 37/06; Y02A 50/30
See application file for complete search history.

(56) References Cited

OTHER PUBLICATIONS

Bieksiene, Kristina et al., "Post COVID-19 Organizing Pneumonia: The Right Time to Interfere", Medicina, 57(283), pp. 1-7 (2021).

Degli Esposti, Luca et al., "The Use of Oral Amino-Bisphosphonates and Coronavirus Disease 2019 (COVID-19) Outcomes", Journal of Bone and Mineral Research, pp. 1-7 (2021).

Sing, Chor-Wing et al., "Nitrogen-Containing Bisphosphonates Are Associated with Reduced Risk of Pneumonia in Patients with Hip Fracture", Journal of Bone and Mineral Research, 35(9):1676-1684 (Jun. 2, 2020).

Pinzon, Miguel Alejandro et al., "Dexamethasone vs. methylprednisolone high dose for Covid-19 pneumonia", PLoS ONE, 16(5):e0252057 (2021).

Xie, Li-Xin, "Interpretation of the 7th edition of the 'diagnosis and treatment guidelines of coronavirus disease 2019 in China': Progress and Challenges", Chronic Diseases and Translational Medicine, 6:75-78 (2020).

Shetty, Gautam M., "Double Trouble—COVID-19 and the Widespread Use of Corticosteroids: Are We Staring at an Osteonecrosis Epidemic?", Indian Journal of Orthopaedics, 56:226-236 (2022).

Brufsky, Adam et al., "Boning up: amino-bisphophonates as immunostimulants and endosomal disruptors of dendritic cell in SARS-COV-2 infection", Journal of Translational Medicine, 18:261 (2020).

Wang, Yingjun et al., "In Vitro Osteogenesis of Synovium Mesenchymal Cells Induced by Controlled Release of Alendronate and Dexamethasone from a Sintered Microspherical Scaffold", Journal of Biomaterials Science, Polymer Edition, pp. 1-14 (Oct. 17, 2014).

* cited by examiner

USE OF A NITROGEN-CONTAINING BISPHOSPHONATE IN COMBINATION WITH A GLUCOCORTICOID IN PREVENTING OR TREATING VIRAL PNEUMONIA

CROSS-REFERENCE TO RELATED APPLICATIONS

The present application claims the priority of Chinese patent application 2021113682916 filed on Nov. 18, 2021, the contents of which are hereby incorporated by reference in its entirety.

FIELD OF THE INVENTION

The present disclosure relates to biological, medical and clinical fields. Specifically, the present disclosure relates to use of a nitrogen-containing bisphosphonate in combination with a glucocorticoid in preventing or treating viral pneumonia.

BACKGROUND OF THE INVENTION

Coronavirus Disease 2019 (COVID-19) is an acute respiratory infectious disease caused by 2019 novel coronavirus (SARS-CoV-2). The main routes of transmission are respiratory droplet transmission and contact transmission, with the incubation period of 1-14 days, mostly 3-7 days.

Typically, COVID-19 is mainly manifested as fever, dry cough and fatigue, and a small number of patients also have nasal congestion, runny nose, diarrhea and other upper respiratory and gastrointestinal symptoms. Patients with severe illness usually have difficulty in breathing after about one week, and in severe cases they rapidly progress to acute respiratory distress syndrome, septic shock, coagulation dysfunction, multiple organ failure and the like, which eventually lead to the death of the patient. SARS-CoV-2 is highly infectious and has a high rate of fatality. The Delta and Omicron strains are currently predominant, which are more infectious or more pathogenic.

SARS-CoV-2 belongs to the Coronaviridae family of the order Nidovirales. The virions are spherical or oval with polymorphism, with a diameter of 60 to 220 nm. The virus has an envelope with spikes on the envelope, and the internal genome is single-stranded positive-stranded RNA. The SARS-CoV-2 viral genome has overlapping open reading frames (ORFs) at about ⅔ from the 5' end. ORF1a and ORF1b are mainly responsible for encoding enzymes related to viral replication and transcription and other nonstructural proteins. The rest ⅓ of the genome is responsible for encoding major structural proteins such as spike protein, envelope membrane protein, membrane protein, and nucleocapsid protein.

The S protein of SARS-CoV-2 has two functional domains: one is the S1 receptor binding domain (RBD), and the other is the S2 domain that mediates the fusion of the virus with host cell membrane. SARS-CoV-2 first binds to the ACE2 receptor on the host cell through the S1 receptor-binding domain. The S1 domain then detach from the viral surface, prompting fusion of the S2 domain with the host cell membrane. This process requires activation of the S protein, which is achieved by cleavage at two sites (S1/S2 and S2') by the proteases Furin and TMPRSS2. The cleavage by Furin at the S1/S2 site can result in a conformational change in the viral S protein, thus exposing the RBD and/or S2 domains. The SARS-CoV-2 virus can also be phagocytosed into macrophages. In the cell, an endosome is firstly formed, and then under the action of CatL, the S protein of the SARS-CoV-2 virus is fused with the endosome, which enters the cytoplasm for replication.

Currently, multiple variants of SARS-CoV-2 have been identified, including the variants Alpha (B.1.1.7), Beta (B.1.351), Gamma (P.1), Epsilon (B.1.427), Delta (B.1.617.2), Delta Plus (AY.4.2), Lambda (C.37), Mu (B.1.621) and Omicron (B.1.1.529). The Delta variant, for example, has slightly decreased pathogenicity but greatly increased infectivity. The mutation rate of SARS-CoV-2 has accelerated over time, posing great challenges to vaccines and neutralizing antibody therapies. The speed of production and inoculation of the COVID-19 vaccines often fall behind the mutation speed of the virus. Therefore, there is a need in the field to explore a novel combination therapy by using the marketed drugs, so as to block the transmission of the virus at early stage of infection.

In the prior art, bisphosphonates are used for treating osteoporosis, osteitis deformans, hypercalcemia and bone pain caused by bone metastases of malignant tumors, especially osteoporosis characterized by "osteopenia and bone structure destruction". However, the effect of bisphosphonates (and/or in combination with other active agents) in viral pneumonia has not been identified in the prior art. Therefore, it is of great necessity to explore unconventional treatment strategies for COVID-19.

SUMMARY OF THE INVENTION

The technical solutions of the present disclosure are at least partially based on the following unexpected findings of the inventor: administration of a nitrogen-containing bisphosphonate in combination with a glucocorticoid can effectively prevent or treat viral pneumonia.

Therefore, the present disclosure provides a method for preventing or treating viral pneumonia, including the following steps: administering to a subject a prophylactically effective amount or a therapeutically effective amount of a nitrogen-containing bisphosphonate and a glucocorticoid; the nitrogen-containing bisphosphonate is selected from any one of the following or a combination thereof: pamidronate, alendronate, risedronate, ibandronate, zoledronate, minodronate and incadronate; the salt is selected from any one of the following or a combination thereof: ammonium, sodium, lithium, potassium, calcium, magnesium, barium, zinc and aluminum salts, salts formed from organic bases and salts formed from basic amino acids; the glucocorticoid is selected from any one of the following or a combination thereof: dexamethasone, rimexolone, prednisolone, fluorometholone, hydrocortisone, mometasone, fluticasone, beclomethasone, flunisolide, triamcinolone, fluticasone propionate, beclomethasone dipropionate, budesonide and mometasone furoate.

The nitrogen-containing bisphosphonate and the glucocorticoid are administered simultaneously or sequentially, wherein the mass ratio of the nitrogen-containing bisphosphonate to the glucocorticoid is 200:1 to 100:1.

The present disclosure also provides a pharmaceutical composition or kit comprising:
- a nitrogen-containing bisphosphonate as defined in the present disclosure,
- a glucocorticoid as defined in the present disclosure, and
- optionally, a pharmaceutically acceptable carrier.

When preparing the pharmaceutical composition or kit, the nitrogen-containing bisphosphonate and the glucocorticoid are in the same container or in different containers. The nitrogen-containing bisphosphonate and the glucocorticoid are independently prepared in liquid or powder form. The amount of the nitrogen-containing bisphosphonate in a unit dose is 1 mg to 100 mg. The amount of the glucocorticoid in a unit dose is 10 μg to 10 mg.

The nitrogen-containing bisphosphonate and the glucocorticoid are independently prepared into any one of the following dosage forms or a combination thereof: injection, spray, aerosol, nasal drop, oral agent and dosage forms suitable for mucosal administration.

BRIEF DESCRIPTION OF THE DRAWINGS

FIG. 3A to FIG. 3C show that alendronate sodium (Alen) combined with dexamethasone (Dex) can down-regulate the expression of inflammatory cytokines IL-1 (FIG. 3A), TNF-α (FIG. 3C) and IL-6 (FIG. 3B) in macrophages infected with Delta strain in vitro. Mock: blank group; PBS: buffer control group.

FIG. 4A to FIG. 4C show that alendronate sodium (Alen) combined with dexamethasone (Dex) can inhibit the replication of SARS-CoV-2 Delta strain in A549-ACE2-overexpressing cell line. Mock: blank group; PBS: buffer control group.

FIG. 5A to FIG. 5E show the effect of alendronate sodium (Alen) combined with dexamethasone (Dex) in treating mice infected with SARS-CoV-2 Delta strain in vivo. HE staining shows that the peribronchial and perivascular inflammatory cell infiltration in mice are reduced in the combined therapy group, and the pathological damage of lung tissue is significantly alleviated (FIG. 5A). PCR shows that the viral load in the lung tissue of mice is reduced (FIG. 5B, FIG. 5C), and the inflammatory factors are down-regulated (FIG. 5D, FIG. 5E) in the combined therapy group. Mock: blank group; PBS: buffer control group.

FIG. 6A to FIG. 6B show that nasal administration of alendronate sodium in combination with dexamethasone significantly increases endosomal pH and improves anti-inflammatory effects, when compared with intravenous administration.

DETAILED DESCRIPTION OF THE INVENTION

Pharmaceutical Use

In view of the above-mentioned needs, the present disclosure provides use of a nitrogen-containing bisphosphonate in combination with a glucocorticoid in the manufacture/preparation of a medicament.

In some embodiments, the medicament is used for any one of the following or a combination thereof: preventing the occurrence or recurrence of viral pneumonia, treating viral pneumonia or symptoms thereof.

The expression "a combination of a nitrogen-containing bisphosphonate and a glucocorticoid" or "a nitrogen-containing bisphosphonate in combination with a glucocorticoid" should be understood broadly and should not be limited to direct physical contact of the two active ingredients during the preparation process of the medicament. (1) In terms of space: in an exemplary technical solution, the nitrogen-containing bisphosphonate and the glucocorticoid are in the same container; in another exemplary technical solution, the nitrogen-containing bisphosphonate and the glucocorticoids are in different containers; in even another exemplary technical solution, the nitrogen-containing bisphosphonate and the glucocorticoid are provided independently in separate forms by different manufacturers. (2) In terms of time: the nitrogen-containing bisphosphonate and the glucocorticoid can be provided concurrently/simultaneously; the nitrogen-containing bisphosphonate and the glucocorticoid can also be provided successively/sequentially.

Bisphosphonates are organic analogs of pyrophosphates, wherein two P—C bonds are linked to the same carbon atom to form an organic compound represented by Formula I characterized by P—C—P structure. Bisphosphonates can be classified into nitrogen-containing bisphosphonates and non-nitrogen-containing bisphosphonates.

Formula I

In some embodiments, the nitrogen-containing bisphosphonate is selected from the group consisting of alendronate, pamidronate, risedronate, ibandronate, zoledronate, minodronate and incadronate.

It should be understood that the term "salt" in the present disclosure refers to acid and/or base addition salts formed with inorganic acids, inorganic bases, organic acids or organic bases. "Salt" may include zwitterions, for example when the compound represented by Formula I comprises both a basic group (such as amine or pyridine or imidazole ring) and an acidic group.

In some embodiments, the compound represented by Formula I is a base addition salt. Exemplary base addition salts are selected from the group consisting of ammonium, alkali metal (such as sodium, lithium, potassium) salts; alkaline earth metal (such as calcium, magnesium) salts; barium, zinc, aluminum salts; salts formed with organic bases (such as amines); salts formed with amino acids (such as arginine, lysine). As an example, when the compound represented by Formula I is alendronate, it can be alendronate sodium; when the compound represented by Formula I is pamidronate, it can be pamidronate sodium.

The term "glucocorticoid" in the present disclosure is a class of steroid hormones secreted by the zona fasciculata in the adrenal cortex, which have the effect of regulating the biosynthesis and metabolism of carbohydrates, fats and proteins. Glucocorticoids include not only endogenous substances, but also artificially synthesized drugs.

In some embodiments, the glucocorticoid is selected from any one of the following or a combination thereof: dexamethasone, rimexolone, prednisolone, fluorometholone, hydrocortisone, mometasone, fluticasone, beclomethasone, flunisolide, triamcinolone, fluticasone propionate, beclomethasone dipropionate, budesonide and mometasone furoate.

In a particular embodiment, the combination of alendronate and dexamethasone is used in preparing a medicament.

In some embodiments, the viral pneumonia that can be prevented or treated with a nitrogen-containing bisphosphonate in combination with a glucocorticoid is associated with or caused by a virus selected from the group consisting of coronavirus, influenza A virus, influenza B virus, influenza C virus, measles virus, mumps virus, respiratory syncytial virus, parainfluenza virus, human hemipulmonary virus, Hendra virus, Nipah virus, rubella virus, rhinovirus, adenovirus, reovirus, Coxsackie virus, ECHO virus, and variants thereof.

In some embodiments, the coronavirus is a virus of the family Coronaviridae or a variant thereof.

In some particular embodiments, the coronavirus is a virus of the genus Coronavirus or a variant thereof.

In some particular embodiments, the virus of the genus Coronavirus is selected from the group consisting of HCoV-229E or variants thereof, HCoV-OC43 or variants thereof, HCoV-NL63 or variants thereof, HCoV-HKU1 or variants thereof, SARS-CoV or variants thereof, SARS-CoV2 or variants thereof and MERS-CoV or variants thereof.

In some particular embodiments, the coronavirus is SARS-CoV2 or a variant thereof.

In some particular embodiments, the SARS-CoV2 variant is selected from any one of the following or a combination thereof: Alpha, Beta, Gamma, Delta, Delta Plus, Epsilon, Lambda, Mu and Omicron.

In some embodiments, the viral pneumonia is selected from any one of the following: mild, moderate, severe and critical.

In some embodiments, the clinical classification of viral pneumonia divides patients into four types:

1) mild: the clinical symptoms are mild, and pneumonia imaging manifestation is not observed.

2) moderate: the patient has fever, respiratory tract symptoms, and pneumonia imaging manifestation can be observed.

3) severe: the patient meets any of the following: respiratory distress, RR≥30 times/min; resting fingertip oxygen saturation ≤93%; arterial partial pressure of oxygen ($PaO_2$)/inhaled oxygen concentration ($FiO_2$)≤300 mmHg (1 mmHg=0.133 kPa). 4) critical: the patient meets one of the following: respiratory failure and in need of mechanical ventilation; shock; combined with failure of other organ(s) and in need of ICU monitoring and treatment.

Formulation of the Nitrogen-Containing Bisphosphonate and the Glucocorticoid

The nitrogen-containing bisphosphonate and the glucocorticoid of the present disclosure can each independently be prepared into powder, liquid solution (for example injectable solution, aqueous or physiological saline solution, or suspension, ointment, droplet, emulsion, gel, syrup, aerosol, spray, nasal drop), tablet, coated tablet, microcapsule, suppository, pill, granule, dragee or capsule. The preparation methods are generally described in Stanley A Plotkin et al., Vaccine 4th edition, W.B. Saunders Company 2003.

The nitrogen-containing bisphosphonate and the glucocorticoid can each independently be prepared into a dosage form selected from the group consisting of injection, spray, aerosol, nasal drop, oral agent and dosage forms suitable for mucosal administration.

In some embodiments, the amount of the nitrogen-containing bisphosphonate in a unit dose is 1 mg to 100 mg. Mention may be made of 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg and 100 mg.

In some embodiments, the amount of the glucocorticoid in a unit dose is 10 μg to 1 mg. Mention may be made of 10 μg, 20 μg, 30 μg, 40 μg, 50 μg, 60 μg, 70 μg, 80 μg, 90 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 2 mg, 3 mg, 4 mg, 5 mg, 6 mg, 7 mg, 8 mg, 9 mg and 10 mg.

In some embodiments, the mass ratio of the nitrogen-containing bisphosphonate and the glucocorticoid is 200:1; 190:1; 180:1; 170:1; 160:1; 150:1; 140:1; 130:1; 120:1; 110:1; 100:1.

The term "unit dose" as used in the present disclosure refers to a physically discrete unit suitable for administration to a subject as a unit dose. Each unit contains a predetermined amount of nitrogen-containing bisphosphonate and/or glucocorticoid which, alone or in combination, presents as an amount sufficient to produce the desired effect.

In some embodiments, the unit dose described in the present disclosure is expressed by volume and is selected from: 0.1 ml, 0.15 ml, 0.2 ml, 0.5 ml, 1.0 ml, 1.5 ml, 2.0 ml, 2.5 ml, 3.0 ml, 4.0 ml, 5.0 ml, 10.0 ml, 20.0 ml, 30.0 ml, 40.0 ml, 50.0 ml, 60.0 ml, 70.0 ml, 80.0 ml, 90.0 ml, 100.0 ml, 150 ml, 200 ml, 250.00 ml, and ranges between any two of the above values.

Those skilled in the art understand that a unit dose that is too large or too small results in clinical inconvenience. Therefore, when the nitrogen-containing bisphosphonate or glucocorticoid of the present disclosure is administered to a human subject by subcutaneous injection, the unit dose is preferably in the range of 0.5 ml to 1.0 ml.

When the nitrogen-containing bisphosphonate or glucocorticoid of the present disclosure is administered to a human subject intranasally, the unit dose is preferably in the range of 0.15 ml to 0.2 ml.

When the nitrogen-containing bisphosphonate or glucocorticoid of the present disclosure is administered to a human subject intravenously, the unit dose is preferably in the range of 30.0 ml to 1000 ml.

It should be understood here that although the unit dose is expressed by volume, this does not mean that the nitrogen-containing bisphosphonate or glucocorticoid or composition thereof of the present disclosure can only be in the form of liquid formulation. When the nitrogen-containing bisphosphonate or glucocorticoid of the present disclosure is prepared into a solid (powder or lyophilized powder) formulation, the volume of a unit dose can represent the volume of liquid which is reconstituted from the powder or lyophilized powder.

Pharmaceutical Composition

According to some embodiments, provided is a pharmaceutical composition comprising a nitrogen-containing bisphosphonate, a glucocorticoid, and optionally a pharmaceutically acceptable carrier.

Suitable pharmaceutically acceptable carriers are described in Remington Pharmaceutical Sciences by E. W. Martin. In particular embodiments, the pharmaceutical composition may further comprise one or more pharmaceutically acceptable carriers, including diluent, excipient, filler, binder, wetting agent, disintegrant, absorption enhancer, surfactant, adsorption carrier, lubricant or synergist and the like conventional in the pharmaceutical field.

Those skilled in the art are able to understand that when the pharmaceutical composition is in the form of powder or lyophilized powder, the difference from the pharmaceutical composition in liquid form lies in the water content and/or buffer environment.

In some embodiments, the nitrogen-containing bisphosphonate is selected from the group consisting of alendronate, pamidronate, risedronate, ibandronate, zoledronate, minodronate and incadronate.

In some embodiments, the glucocorticoid is selected from any one of the following or a combination thereof: dexamethasone, rimexolone, prednisolone, fluorometholone, hydrocortisone, mometasone, fluticasone, beclomethasone, flunisolide, triamcinolone, fluticasone propionate, beclomethasone dipropionate, budesonide and mometasone furoate.

In some embodiments, the nitrogen-containing bisphosphonate and the glucocorticoid are in the same container or in different containers.

In some embodiments, the pharmaceutical composition is for use in any one of the following or a combination thereof: preventing the occurrence or recurrence of viral pneumonia, treating viral pneumonia or symptoms thereof.

In some embodiments, the virus is selected from any one of the following or a combination thereof: coronavirus, influenza A virus, influenza B virus, influenza C virus, measles virus, mumps virus, respiratory syncytial virus, parainfluenza virus, human hemipulmonary virus, Hendra virus, Nipah virus, rubella virus, rhinovirus, adenovirus, reovirus, Coxsackie virus, ECHO virus, and variants thereof.

In some embodiments, the coronavirus is a virus of the family Coronaviridae or a variant thereof.

In some particular embodiments, the coronavirus is a virus of the genus Coronavirus or a variant thereof.

In some particular embodiments, the virus of the genus Coronavirus is selected from the group consisting of HCoV-229E or variants thereof, HCoV-OC43 or variants thereof, HCoV-NL63 or variants thereof, HCoV-HKU1 or variants thereof, SARS-CoV or variants thereof, SARS-CoV2 or variants thereof and MERS-CoV or variants thereof.

In some particular embodiments, the coronavirus is SARS-CoV2 or a variant thereof.

In some particular embodiments, the SARS-CoV2 variant is selected from any one of the following or a combination thereof: Alpha, Beta, Gamma, Delta, Delta Plus, Epsilon, Lambda, Mu and Omicron.

In some embodiments, the viral pneumonia is selected from any one of the following: mild, moderate, severe and critical.

In some embodiments, the pharmaceutical composition is in a dosage form selected from the group consisting of injection, spray, aerosol, nasal drop, oral agent and dosage forms suitable for mucosal administration.

In some embodiments, the nitrogen-containing bisphosphonate and the glucocorticoid can be formulated into the same dosage form or different dosage forms.

Methods for Preventing or Treating

According to some embodiments, provided is a method for preventing or treating viral pneumonia, which includes administering to a subject a prophylactically effective amount or a therapeutically effective amount of a nitrogen-containing bisphosphonate and a glucocorticoid.

In some embodiments, routes of administration that may be mentioned include, but are not limited to: intramuscular, intravenous, subcutaneous, intradermal, oral, intranasal, respiratory, transmucosal, sublingual and parenteral.

In some embodiments of the method according to the present disclosure, an "effective amount" or "effective dose" refers to the amount of a medicament, compound or pharmaceutical composition necessary to obtain any one or more beneficial or desired results. The beneficial or desired results include, but are not limited to improving clinical outcomes (such as reducing morbidity, mortality, improving one or more symptoms), reducing severity, delaying the onset of the condition (including the condition or complication thereof, intermediate pathological phenotype, biochemistry, histology and/or behavioral symptoms that appears during the developmental process of the condition).

The beneficial or desired result can be prophylactic in the sense of completely and/or partially preventing the disease or symptoms thereof; or can be therapeutic in the sense of completely and/or partially stabilizing or curing the disease and/or the negative effects caused by the disease.

The amount of medicament required for a single administration to a subject can be conveniently obtained by calculating the mathematical product of subject's body weight×the dose per unit body weight required for a single administration to the subject. For example, in the process of preparing a medicament, it is generally considered that the body weight of an adult is 50 kg to 70 kg, and the dose can be initially determined from the equivalent dose conversion relationship between the experimental animal and human. For example, it can be determined according to the guidances provided by the FDA, SFDA and other drug regulatory agencies, or refer to literatures (such as Huang Ji-han et al., Dose conversion among different animals and healthy volunteers in pharmacological study, Chinese Journal of Clinical Pharmacology and Therapeutics, 2004; 9:1069-1072).

In exemplary embodiments of the present disclosure, the doses for human and mouse can be converted according to the body surface area conversion factor of 0.0026 for human and mouse.

In exemplary embodiments of the present disclosure, the nitrogen-containing bisphosphonate is administered to mice with body weight of 18 to 22 g at an amount of 150 μg/mouse.

In exemplary embodiments of the present disclosure, the glucocorticoid is administered to mice with body weight of 18 g to 22 g at an amount of 150 μg/mouse.

According to some embodiments, also provided is a method for preventing respiratory viral pneumonia from becoming severer in a subject, said method includes the step of administering a nitrogen-containing bisphosphonate and/or a glucocorticoid to a subject with respiratory viral pneumonia (or a subject having a tendency of developing severe/critical illness); preferably, the nitrogen-containing bisphosphonate and/or the glucocorticoid is/are administered by oral, intranasal or respiratory administration.

In some embodiments, the order of administration of the nitrogen-containing bisphosphonate and the glucocorticoid can be concurrent, or one after the other; the order of administration of the two can be interchanged.

According to the present disclosure, the amount of the nitrogen-containing bisphosphonate and the glucocorticoid in the formulation can be adjusted as needed to facilitate administration to subjects with different severity of viral pneumonia.

In some embodiments, the subject is a subject susceptible to viral infection.

In some embodiments, the subject is a carrier of the virus.

In some embodiments, the subject is a subject who has developed symptoms due to the presence of the virus.

In some embodiments, the subject is a subject who might develop symptoms due to the presence of the virus.

In some embodiments, the subject is a subject at risk of developing severe or critical illness.

In some embodiments, the subject is administered with a nitrogen-containing bisphosphonate or a glucocorticoid (independently, or in combination) at the following frequency: 1 to 4 times every 4 years, 1 to 3 times every 3 years, 1 to 2 times every 2 years, 1 time a year, 2 times a year, 3 times a year, 4 times a year, 5 times a year, 6 times a year, 1 time a month, 2 times a month, 3 times a month, 4 times a month, 5 times a month, 6 times a month, 7 times a month, 8 times a month, 1 time a week, 2 times a week, 3 times a week, 4 times a week, 5 times a week, 6 times a week, 1 time every three days, 2 times every three days, 3 times every three days, 1 time every two days, 2 times every two days, 1 time a day, 2 times a day.

In some embodiments, the frequency of administration of the nitrogen-containing bisphosphonate and the glucocorticoid can be the same or different.

In some embodiments, the time interval between each administration is the same or different.

In some exemplary embodiments, when the nitrogen-containing bisphosphonate and the glucocorticoid are not administered concurrently, the interval between the two does not exceed a limit such that the nitrogen-containing bisphosphonate and the glucocorticoid can exert a synergistic effect in the subject. Those skilled in the art can determine such intervals according to the pharmacokinetic profile of the active ingredient. As an example, the administration interval between the nitrogen-containing bisphosphonate and the glucocorticoid is 48 hours to 1 hour; for example no more than 48 hours, no more than 47 hours, no more than 46 hours, no more than 45 hours, no more than 44 hours, no more than 40 hours, no more than 36 hours, no more than 30 hours, no more than 24 hours, no more than 20 hours, no more than 15 hours, no more than 12 hours, no more than 11 hours, no more than 10 hours, no more than 9 hours, no more than 8 hours, no more than 7 hours, no more than 6 hours, no more than 5 hours, no more than 4 hours, no more than 3 hours, no more than 2 hours, or 1 hour. When the two are administered within 1 hour one after the other, they can be seen as administered concurrently.

The present disclosure provides a method for preventing or treating a coronavirus infection, which includes administering to a subject a prophylactically effective amount or a therapeutically effective amount of a nitrogen-containing bisphosphonate and a glucocorticoid; or administering a prophylactically effective amount or a therapeutically effective amount of pharmaceutical composition.

In some embodiments, the administration of the nitrogen-containing bisphosphonate or glucocorticoid or pharmaceutical composition thereof is systemic or topical.

In some embodiments, the nitrogen-containing bisphosphonate or glucocorticoid or pharmaceutical composition thereof is administered by parenteral (such as intramuscular, intraperitoneal, intravenous, subcutaneous, intradermal) injection.

In some embodiments, the nitrogen-containing bisphosphonate or glucocorticoid or pharmaceutical composition thereof is administered intramuscularly.

In other embodiments, the nitrogen-containing bisphosphonate or glucocorticoid or pharmaceutical composition thereof is delivered intradermally (for example in a manner that does not disrupt the epithelial cell barrier by mechanical devices).

In some other embodiments, the nitrogen-containing bisphosphonate or glucocorticoid or pharmaceutical composition thereof is administered by rectal, vaginal, nasal, oral, sublingual, respiratory, ocular or transdermal routes.

In some embodiments, the nitrogen-containing bisphosphonate or glucocorticoid or pharmaceutical composition thereof is administered as nasal drops.

In some embodiments, the means of an insufflator, nebulizer, pressurized package or introduction of gaseous spray may be used for administration by inhalation. The pressurized package can have a suitable propellant (such as dichlorodifluoromethane, trichloromonofluoromethane, dichlorotetrafluoroethane, carbon dioxide). In the case of using pressurized aerosol, the unit dose can be determined by providing an air valve. Powdered mixtures can be held in the form of unit dose in capsules and cartridges, or, for example in gelatin packets; the powder can be administered from these containers by means of an inhaler or insufflator. For nasal administration, the nitrogen-containing bisphosphonate or glucocorticoid or pharmaceutical composition thereof can be administered in liquid spray or nasal drop formulations, for example via a nebulizer.

In some embodiments, the subject is preferably a mammal, such as a monkey, more preferably a human.

Kit

According to another aspect of the present disclosure, provided is a kit for performing the above method for preventing or treating, comprising at least one container that independently contains a nitrogen-containing bisphosphonate or glucocorticoid or pharmaceutical composition thereof. The composition and/or amount in different containers can be the same or different.

In some embodiments, the nitrogen-containing bisphosphonate or glucocorticoid or pharmaceutical composition thereof of the present disclosure is formulated in a sterile liquid and contained in a sterile container (such as tube, vial, ampoule, syringe).

In some other embodiments, the nitrogen-containing bisphosphonate or glucocorticoid or pharmaceutical composition thereof of the present disclosure is contained in a container in the form of powder or lyophilized powder. It is reconstituted into liquid form just before use.

In an exemplary embodiment, the kit of the present disclosure further comprises one selected from the following or a combination thereof: a needle, water for injection, and instruction for use.

In an exemplary embodiment, the kit of the present disclosure further comprises one selected from the following or a combination thereof: a nebulizer, and instruction for use.

In an exemplary embodiment, the kit of the present disclosure further comprises one selected from the following or a combination thereof: a nasal dropper, and instruction for use.

In the present specification, when describing a numerical range, the expressions " . . . to . . . ", "within the range of . . . " or "between the range of . . . " are used to include the endpoint values.

In the present specification, when describing a numerical range, expressions such as "1 mg to 100 mg" are a abbreviated way of expression and should be deemed as explicitly referring to any decimal or integer within the range.

In the present specification, when describing numerical values (unless otherwise specified), statistical errors and errors introduced by operations should be included. The extent of error depends on the specific situation, for example as for the amount of administration, weighing errors, errors introduced in the formulation process and the like are involved, for example 150 μg can be understood as 150 μg±10%.

In the present specification, unless otherwise specified, "a/an" and "the" should be understood to encompass both singular and plural forms.

EXAMPLES

Unless otherwise specified, the operations on experimental animals of the present disclosure were performed in accordance with the "Regulations for the Administration of Affairs Concerning Experimental Animals", "Guide for the Care and Use of Laboratory Animals", and National Standard GB/14925.

The experimental mice were female ICR, hACE2 transgenic mice, 6-8 weeks old, purchased from the Medical Laboratory Animal Center of the Chinese Academy of Medical Sciences (Beijing). Animal studies of SARS-CoV-2 Delta strain were performed in an animal biosafety level 3 (BASL3) facility using HEPA filter isolators. The studies on mice without viral infection were approved by the ethics committee.

The cells used were mouse primary alveolar macrophages (cultured with 1640 containing 10% fetal bovine serum), A549-ACE2-over-expressing human lung adenocarcinoma cell line (cultured with DMEM medium containing 10% fetal bovine serum). The A549 human lung adenocarcinoma cell line was purchased from the Cell Resource Center, Institute of Basic Medicine, Chinese Academy of Medical Sciences.

Example 1. Alendronate Sodium Combined with Dexamethasone can Increase the Endosomal pH of Macrophages Both In Vitro and In Vivo 1. Experimental Steps In vitro pH measurement: Mouse alveolar macrophages were plated in small dishes at $5 \times 10^4$ cells per well, for confocal study. Then 1 mL of 50 μM alendronate sodium, or 0.2 μM dexamethasone, or a combination of both was added to each well and cultured for 24 h. Then pHrodo™ Red dextran was added for labeling for 10 min, and a confocal microscope was used for imaging.

In vivo pH measurement: each mouse was intranasally administered 150 μg alendronate sodium, or 1 μg dexamethasone, or a combination of both. After 24 hours, alveolar macrophages of the mice were collected and labeled with 50 μg/mL pHrodo™ Red dextran for 10 min, and then detected by Attune® NxT Acoustic Focusing Flow Cytometer.

2. Experimental Results

Figure 1A:
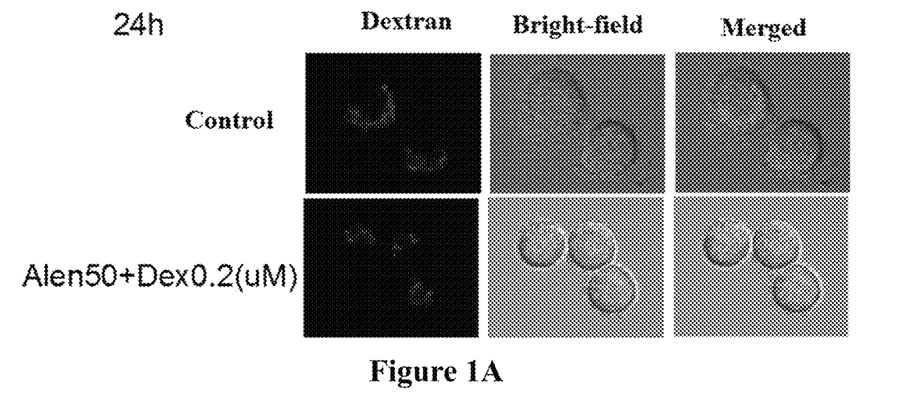
FIG. 1A to FIG. 1D show that alendronate sodium (Alen) combined with dexamethasone (Dex) can increase the endosomal pH of macrophages both in vitro and in vivo. PBS: buffer control group.
Figure 1B:
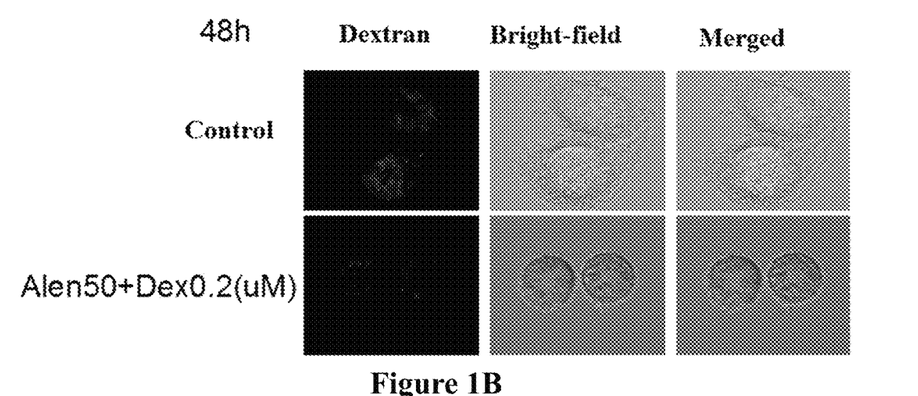
Figure 1C:
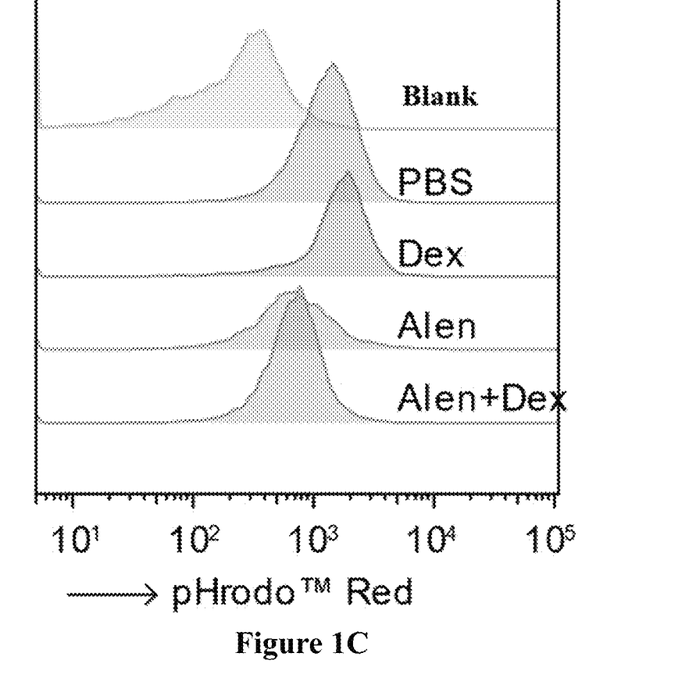
Figure 1D:
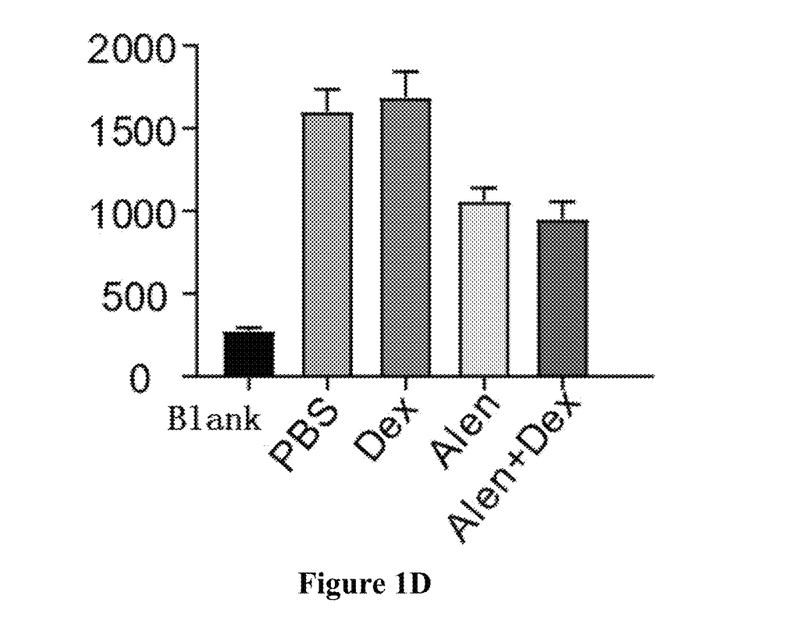

In vitro treatment of mouse alveolar macrophages with alendronate sodium combined with dexamethasone can increase the endosomal pH of the macrophages (FIG. 1A: 24 h, FIG. 1B: 48 h). In vivo administration of alendronate sodium combined with dexamethasone can also increase the endosomal pH of mouse alveolar macrophages (FIG. 1C, FIG. 1D).

Example 2. Alendronate Sodium Combined with Dexamethasone can Promote Clearance of SARS-CoV-2 Delta Strain by Macrophages In Vitro 1. Experimental Steps Mouse alveolar macrophages were plated in a 24-well plate at $5 \times 10^4$ cells per well. On the next day, after virus infection at $2.5 \times 10^4$ TCID50 for 2 h, the medium was discarded, the plate was washed twice with PBS and the PBS was completely discarded during the last wash. 1 mL of 50 μM alendronate sodium, or 0.2 μM dexamethasone, or a combination of both was added to each well; and cultured for 22 h or 46 h. Then the plate was washed twice with PBS and the PBS was completely discarded during the last wash. 1 mL of TRIZOL was added to each well and RNA was extracted and reverse transcribed. The copy numbers of viral genes ORF1ab (FIG. 2B) and N (FIG. 2A) were analyzed by qPCR.

2. Experimental Results

Figure 2A:
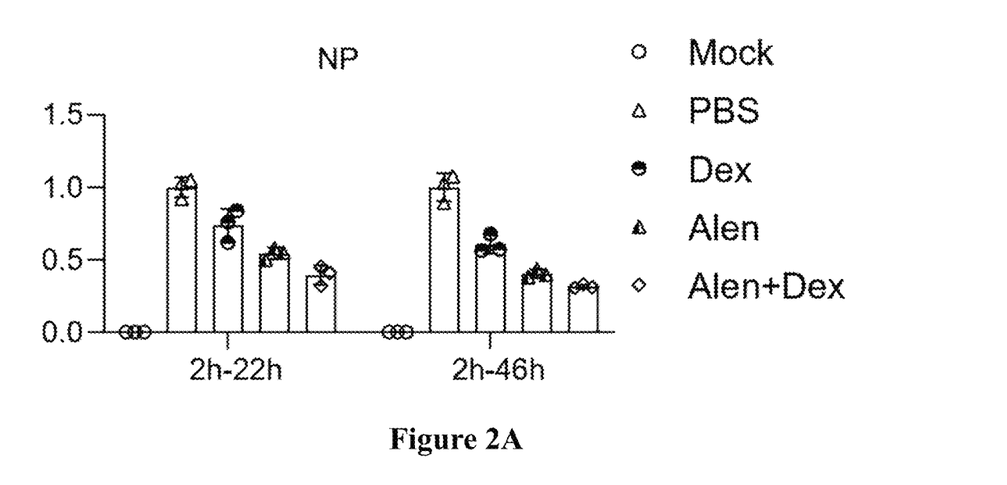
FIG. 2A to FIG. 2B show that alendronate sodium (Alen) combined with dexamethasone (Dex) can promote clearance of SARS-CoV-2 Delta strain by macrophages in vitro. Mock: blank group; PBS: buffer control group.
Figure 2B:
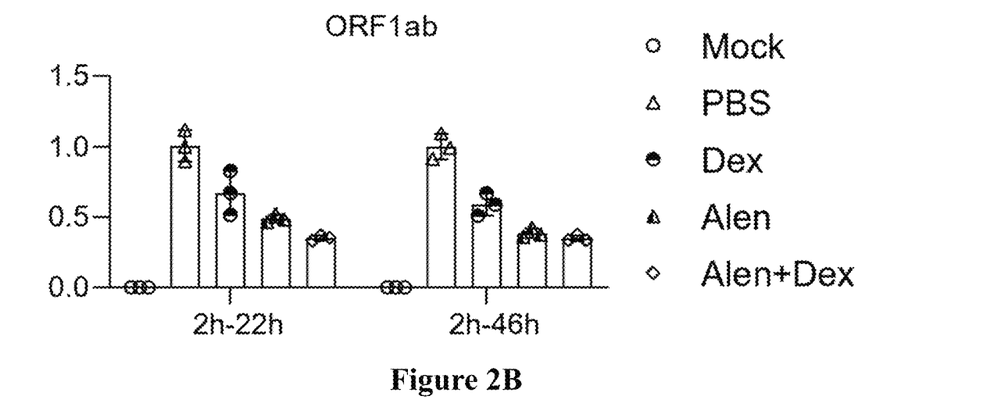

The qPCR analysis shows that alendronate sodium combined with dexamethasone can reduce the viral load of SARS-CoV-2 Delta strain in macrophages in vitro (FIG. 2A and FIG. 2B).

Example 3. Alendronate Sodium Combined with Dexamethasone can Down-Regulate In Vitro the Expression of Inflammatory Cytokines IL-1, TNF-α and IL-6 in Macrophages Infected with Delta Strain 1. Experimental Steps Mouse alveolar macrophages were plated in a 24-well plate at $5 \times 10^4$ cells per well. On the next day, after virus infection at $2.5 \times 10^4$ TCID50 for 2 h, the medium was discarded, the plate was washed twice with PBS and the PBS was completely discarded during the last wash. 1 mL of 50 μM alendronate sodium, or 0.2 μM dexamethasone, or a combination of both was added to each well, and cultured for 22 h or 46 h. Then the plate was washed twice with PBS and the PBS was completely discarded during the last wash. 1 mL of TRIZOL was added to each well and RNA was extracted and reverse transcribed. The expression of IL-6 was analyzed by qPCR.

2. Experimental Results

Figure 3A:
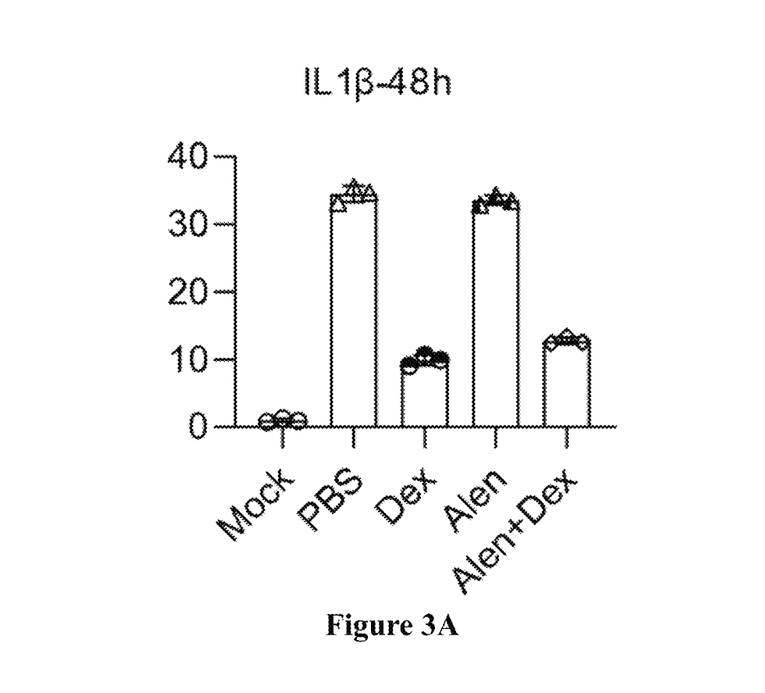
Figure 3B:
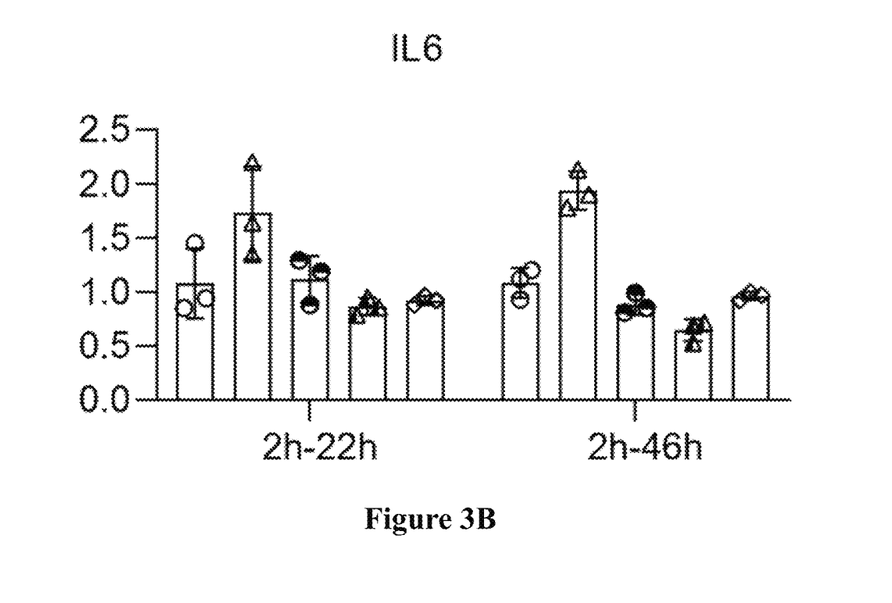
Figure 3C:
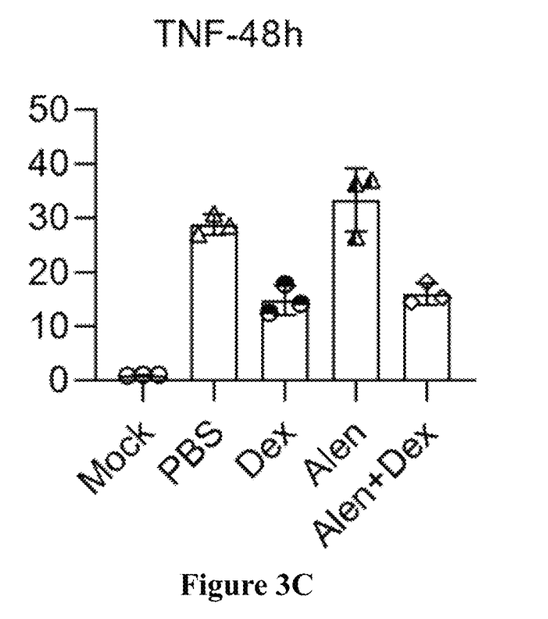

Alendronate sodium combined with dexamethasone can down-regulate the expression of IL-6, IL-1 and TNF-α in macrophages infected with Delta strain (FIG. 3A to FIG. 3C), in vitro.

Example 4. Alendronate Sodium Combined with Dexamethasone can Inhibit the Replication of SARS-CoV-2 Delta Strain in A549-ACE2-Over-Expressing Cell Line 1. Experimental Steps A549-ACE2-over-expressing cell line: The human ACE2 coding sequence was amplified and inserted into plasmid pLV-EF1α-IRES-Puro, which was transiently expressed in 293T cells to obtain viruses containing the target gene. The hACE2-containing lentivirus was transduced into A549 cells, which were then screened with 1 μg/ml puromycin to obtain clones with high ACE2 expression.

A549-ACE2-over-expressing cells were plated in a 24-well plate at $5 \times 10^4$ cells per well. On the next day, after virus infection at $2.5 \times 10^4$ TCID50 for 4 h, the medium was discarded, the plate was washed twice with PBS and the PBS was completely discarded during the last wash. 1 mL of 50 μM alendronate sodium, or 0.2 μM dexamethasone, or a combination of both was added to each well, and cultured for 20 h. Then the plate was washed twice with PBS and the PBS was completely discarded during the last wash. 1 mL of TRIZOL was added to each well and RNA was extracted and reverse transcribed. The copy numbers of viral genes ORF1ab (FIG. 4B) and N (FIG. 4A) were analyzed by qPCR. 1 mL of cell fixative was added to each well, and the N protein was labeled by immunofluorescence staining (Abcam, Cat. Ab273434, 1:200).

2. Experimental Results

Figure 4A:
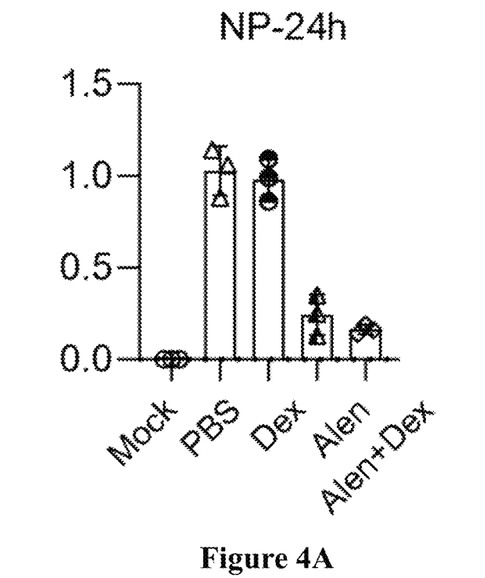
Figure 4B:
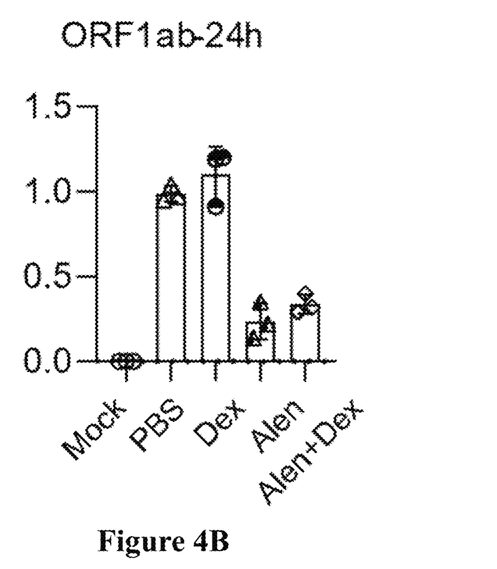
Figure 4C:
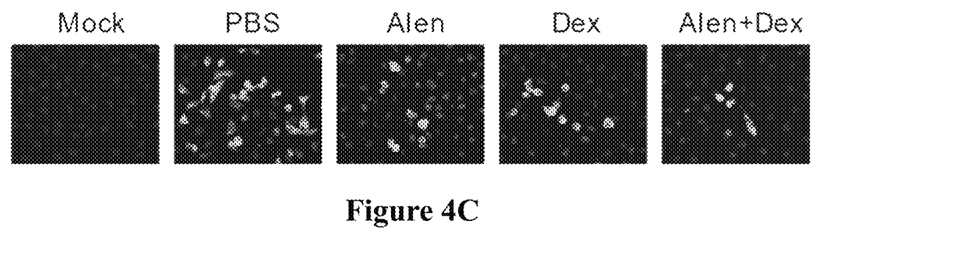

Alendronate sodium combined with dexamethasone can reduce the copy number of Delta in A549-ACE2-over-expressing cells (FIG. 4A, FIG. 4B). Alendronate sodium combined with dexamethasone can reduce the expression of Delta N protein in A549-ACE2-over-expressing cells (FIG. 4C).

Example 5. In Vivo Efficacy of Alendronate Sodium Combined with Dexamethasone in Treating SARS-CoV-2 Delta Strain Infections 1. Experimental Steps The hACE2 transgenic mice were infected intratracheally with SARS-CoV-2 Delta strain ($1\times10^5$ TCID50), and then treated with control group (PBS) or alendronate sodium (150 μg/mouse) or dexamethasone (1 μg/mouse) or a combination of both. The treatment was provided once a day for 5 consecutive days (n=4 mice/group). After 5 days of treatment, the mice were sacrificed, and the lung tissues were fixed for HE staining or put in TRIZOL for lysis.

2. Experimental Results

Figure 5A:
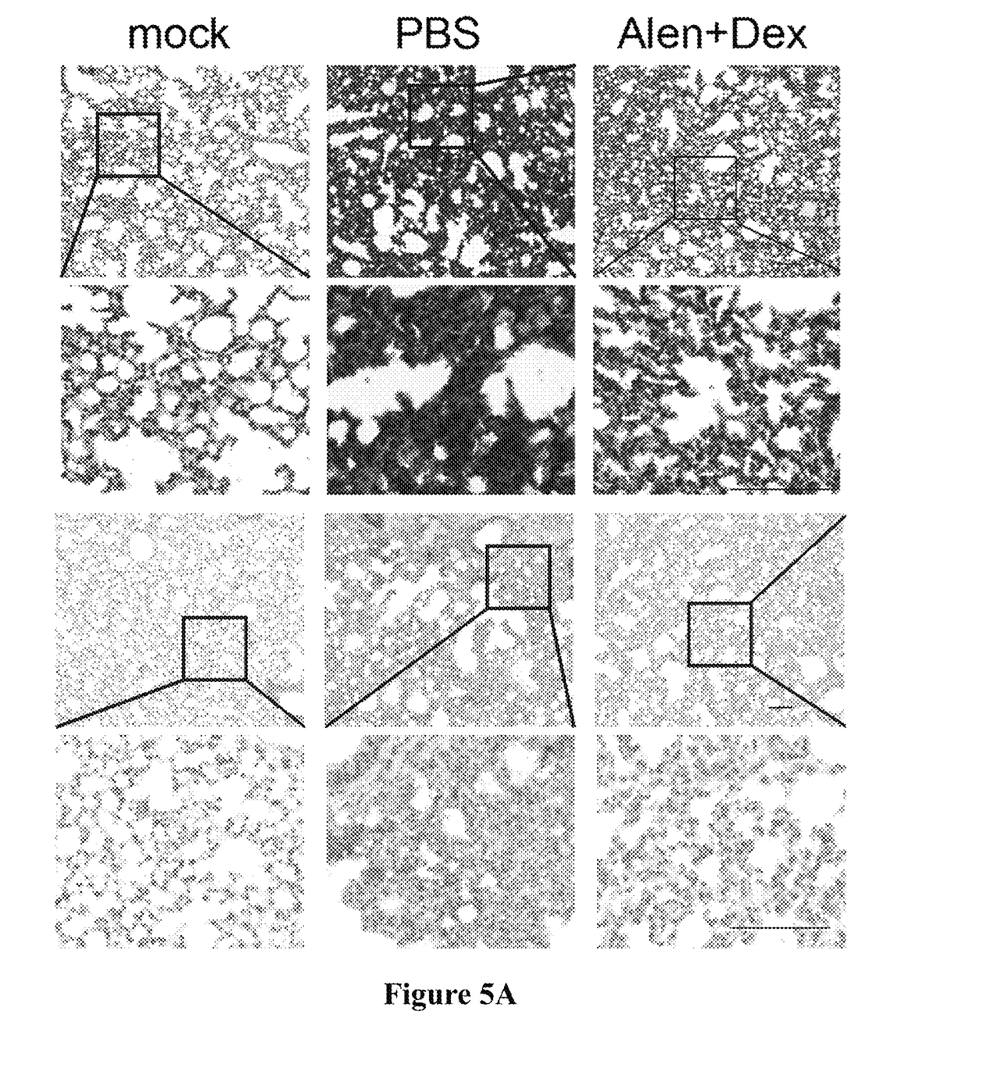

The H&E staining results of mice in the treatment group of alendronate sodium combined with dexamethasone show relatively less lung tissue damage caused by the virus, and the immunohistochemical results show decreased inflammatory cell infiltration (FIG. 5A).

Figure 5B:
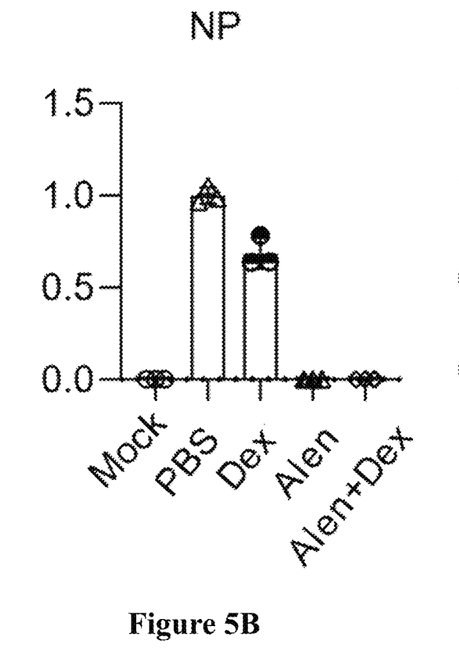
Figure 5C:
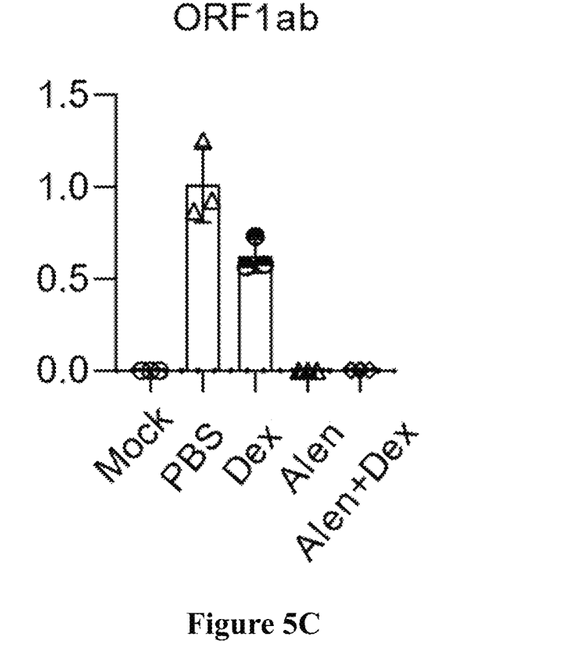

The qPCR results of mice in the treatment group of alendronate sodium combined with dexamethasone show decreased viral load in lung tissues (FIG. 5B (N), FIG. 5C (ORF)).

Figure 5D:
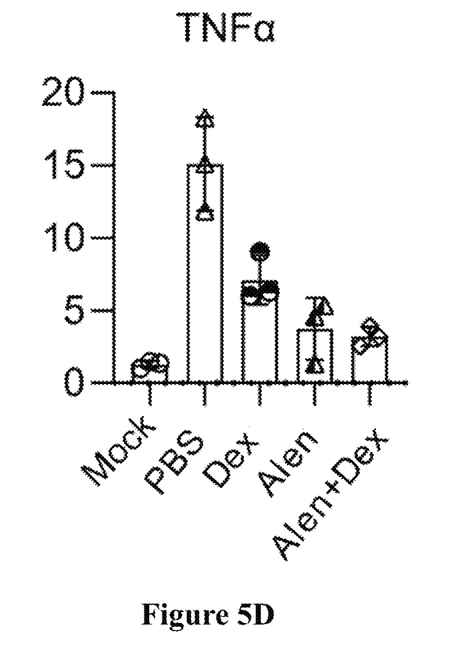
Figure 5E:
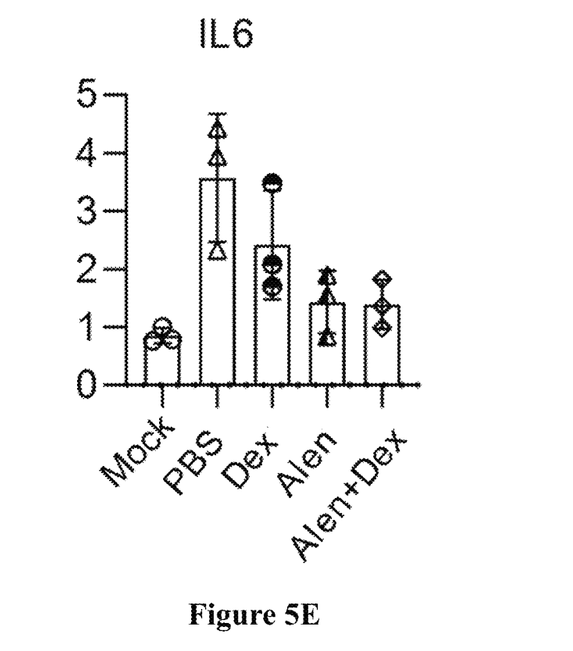

The qPCR results of mice in the treatment group of alendronate sodium combined with dexamethasone show that the expressions of inflammatory factors IL-6 (FIG. 5E) and TNFα (FIG. 5D) are also significantly decreased.

Example 6. Effects of Nasal and Intravenous Administration on Endosomal pH and Anti-Inflammation 1. Experimental Steps After stimulating mice with LPS (100 μg/mouse) for 4 h, alendronate sodium and dexamethasone were intratracheally or intravenously administered to the mice. Alveolar macrophages were collected 20 h later for detection of endosomal pH and expression of the inflammatory factor IL-6.

2. Experimental Results

Figure 6A:
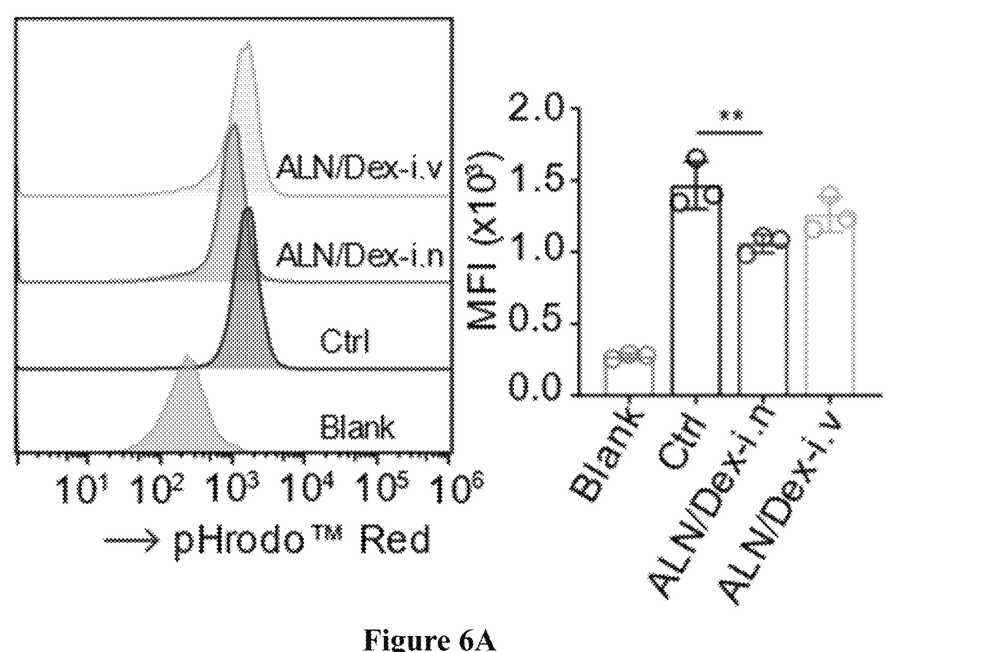
Figure 6B:
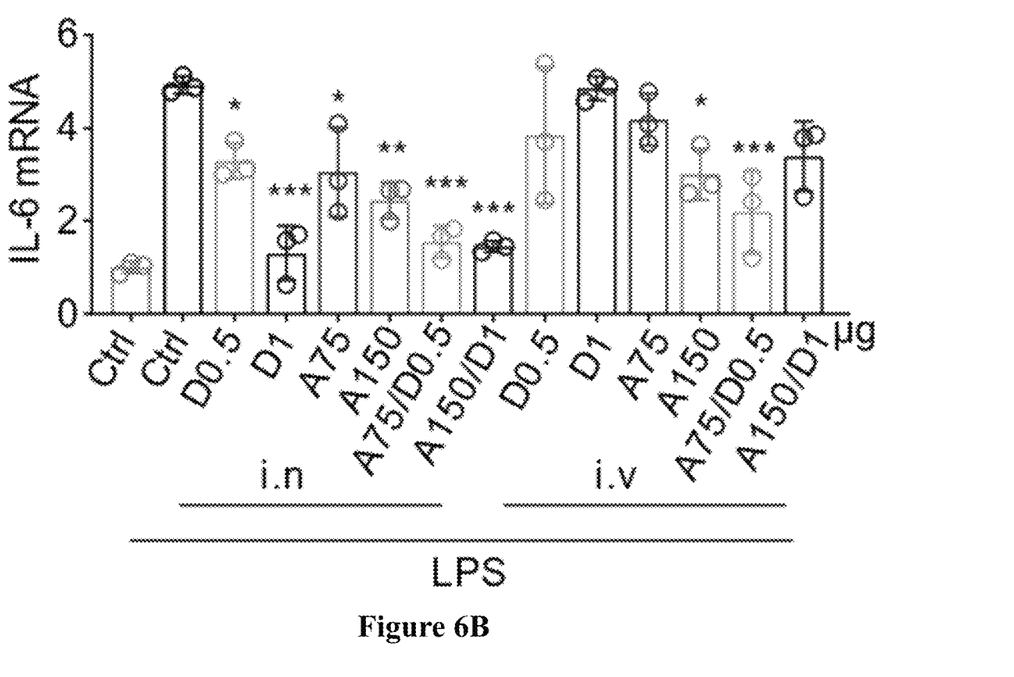

Higher endosomal pH can be observed in mice in the nasal administration group of alendronate and dexamethasone (FIG. 6A); IL-6 expression was lower in the nasal group than that in the intravenous group, under the same conditions (FIG. 6B).

In summary, the solution of the present disclosure has at least the following effects:

1. Nitrogen-containing bisphosphonates can be used for treating SARS-CoV-2 infections (including the Delta strain). It is a new therapeutic strategy for enhancing the clearance of SARS-CoV-2 by alveolar macrophages and inhibiting inflammation.
2. Before and after virus infection, intratracheal administration of nitrogen-containing bisphosphonate inhibits virus replication in macrophages and epithelial cells and enhances the clearance of SARS-CoV-2 by macrophages, by regulating the endosomal pH of macrophages. Therefore, clinical treatment of COVID-19 is achieved; the solution of the present disclosure can effectively reduce the mortality rate of COVID-19 patients and has good prospects of clinical application.
3. The nitrogen-containing bisphosphonates and glucocorticoids of the present disclosure are safe drugs that have been approved by the FDA. Therefore, they have high safety and low toxicity and side effects, and can be applied to the human body.
4. The present disclosure found that alendronate sodium combined with dexamethasone can increase the acidity of macrophage endosomes, limit the replication of SARS-CoV-2 virus in macrophages, and promote virus degradation by macrophages; inhibit the release of inflammatory cytokines (such as IL-1, TNF-α, IFN-γ, IL-6) by macrophages after SARS-CoV-2 virus infection; inhibit the proliferation of SARS-CoV-2 virus in alveolar epithelial cells. In vivo studies have found that compared with the blank control group, alendronate sodium combined with dexamethasone can greatly reduce the pathological damage and viral load in the lung of model animals.

What claimed is:

1. A method of preventing or treating viral pneumonia, including the following steps:
   administering to a subject a prophylactically effective amount or a therapeutically effective amount of alendronate in combination with dexamethasone, wherein:
   the amount of the alendronate in a unit dose is 1 mg to 100 mg;
   the amount of the dexamethasone in a unit dose is 10 μg to 10 mg;
   the mass ratio of the alendronate to the dexamethasone is 200:1 to 100:1;
   the virus is SARS-COV2 or a variant thereof;
   the alendronate and the dexamethasone are prepared into any one of the following dosage forms or a combination thereof: spray, aerosol, nasal drop;
   the alendronate and the dexamethasone are in the same container or in different containers; and
   the alendronate and the dexamethasone are administered simultaneously or sequentially.

2. The method according to claim 1, wherein the SARS-CoV2 variant is selected from any one of the following or a combination thereof: Alpha, Beta, Gamma, Delta, Delta Plus, Epsilon, Lambda, Mu and Omicron.

3. The method according to claim 1, wherein the manifestation of treatment is selected from any one of the following or a combination thereof:
   increasing the endosomal pH of macrophages, limiting virus replication in macrophages, promoting virus degradation in macrophages, inhibiting the release of inflammatory factor from macrophages, inhibiting the release of inflammatory factor from alveolar epithelial cells, inhibiting virus proliferation in alveolar epithelial cells, reducing lung damage, reducing cytokine storm, improving survival rate and prolonging survival period; and
   the inflammatory factor is selected from any one of the following or a combination thereof: IL-1, TNF-α, IFN-γ and IL-6.

4. The method according to claim 1, wherein the manifestation of prevention is selected from any one of the following or a combination thereof: delaying or preventing disease from progression to severe or critical illness, and reduce the risk of progression to severe or critical illness.

5. The method according to claim 1, wherein the viral pneumonia is selected from any one of the following: mild, moderate, severe and critical.

6. The method according to claim 1, wherein the subject is a mammal suffering from, suspected of suffering from, or susceptible to viral pneumonia.

7. The method according to claim 1, wherein the unit dose is in the range of 0.15 ml to 0.2 ml.

8. The method according to claim 1, wherein the alendronate is formulated into a salt selected from the group consisting of: ammonium, sodium, lithium, potassium, calcium, magnesium, barium, zinc and aluminum salts, salts formed from organic bases and salts formed from basic amino acids.

9. The method according to claim 8, wherein the alendronate salt is alendronate sodium.

10. The method according to claim 1, wherein the alendronate and the dexamethasone are administered nasally using nasal drops or liquid spray.

11. The method according to claim 1, wherein the alendronate and the dexamethasone are administered by inhalation using an insufflator, nebulizer, pressurized packaged or introduction of gaseous spray.

12. The method of claim 6, wherein the subject is a human.

13. The method of claim 1, wherein the alendronate and the dexamethasone are in the same container.

14. The method of claim 1, wherein the alendronate and the dexamethasone are administered sequentially.

* * * * *